United States Patent [19]
Hoke et al.

[11] Patent Number: 5,585,479
[45] Date of Patent: Dec. 17, 1996

[54] ANTISENSE OLIGONUCLEOTIDES DIRECTED AGAINST HUMAN ELAM-I RNA

[75] Inventors: Glenn D. Hoke, Mt. Airy; Matthews O. Bradley, Laytonsville, both of Md.; Taffy J. Williams, Lansdale, Pa.; Che-Hung Lee, Silver Spring, Md.

[73] Assignee: The United States of America as represented by the Secretary of the Navy, Washington, D.C.

[21] Appl. No.: 136,741

[22] Filed: Oct. 12, 1993

Related U.S. Application Data

[63] Continuation-in-part of Ser. No. 918,260, Jul. 24, 1992, abandoned.

[51] Int. Cl.⁶ ...................................................... C07H 21/04
[52] U.S. Cl. ...................... 536/24.5; 536/23.1; 536/23.5; 935/34
[58] Field of Search ............................... 514/44; 536/23.1, 536/24.5, 23.5

[56] References Cited

U.S. PATENT DOCUMENTS 5,272,263  12/1993  Hession et al. ..................... 536/23.5

OTHER PUBLICATIONS

E Uhlmann et al (1990) Chemical Reviews 90:544–584.
T Collins et al (1991) J Biol Chem 266:2466–2473.
C P Leamon et al (1991) Proc Natl Acad Sci USA 88:5572–5576.
P L Felgner et al (1987) Proc Natl Acad Sci USA 84:7413–7417.
S Kawai et al (1984) Mol Cell Biol 4:1172–1174.
R Weiss (1991) Science News 139: 108–109.
C A Stein et al (1993) Science 261: 1004–1012.
R W Wagner (1994) Nature 372: 333–335.
S Wu-Pong (1994) Pharmaceutical Technology 118: 102–114.
N Miller et al (1994) Parasitology Today 10: 92–97.
R A Stull et al (1995) Pharmaceutical Research 12: 465–483.

*Primary Examiner*—Bruce R. Campell
*Attorney, Agent, or Firm*—A. D. Spevack, Esq.; William Garvert, Esq.

[57] ABSTRACT

The present invention provides a method for the treatment of septic shock and inflammatory complications of shock. A process for selectively inhibiting the expression of the human ELAM-I mRNA transcript using at least one oligonucleotide which is substantially complementary to at least a portion of the ELAM-I gene is disclosed, as are composition comprising the oligonucleotide.

13 Claims, 2 Drawing Sheets

ANTISENSE OLIGONUCLEOTIDES DIRECTED AGAINST HUMAN ELAM-I RNA

RELATED APPLICATION

This application is a continuation-in-part of application 07/918,260, filed 24 Jul. 1992, which was abandoned after the filing of this application.

BACKGROUND OF THE INVENTION

1. Field of the Invention

This invention relates to agents and therapy to lessen morbidity and mortality by protecting against septic shock, Adult Respiratory Distress Syndrome (ARDS), and other inflammatory complications of shock. Particularly, this invention relates to the treatment of septic shock and the other complications resulting from septic shock by down-regulating the expression of certain cell-cell adhesion receptors or ligands involved in the inflammatory response during septic shock. More specifically, this invention relates to therapy with antisense oligonucleotides which reduce expression of adhesive proteins and protect against septic shock and reduce associated inflammatory damage (like ARDS). Particularly this invention relates to the use of antisense oligonucleotides complementary to human mRNAs or pre-mRNAs coding for ELAM-1 (Endothelial Leukocyte Adhesion Molecule-1) to be used in a therapeutic treatment of sepsis (henceforth to include sepsis, the sepsis syndrome, septic shock and all other manifestations of the sepsis disease, including but not inclusive of, adult respiratory distress syndrome, multi-organ failure, or cardiovascular dysfunction). Mediators of sepsis produce endothelial dysfunctions that result in the development of an intravascular inflammatory response and subsequent damage to the endothelial cells with migration of leukocytes into the surrounding tissues. This invention also relates to the treatment of sepsis with antisense oligonucleotides targeted to cellular based receptors or their ligands where these receptors or ligands are involved in the inflammatory response during the development of sepsis. This invention further relates to the use of antisense oligonucleotides to inhibit the synthesis of ELAM-1, which is responsible for the adhesion of leukocytes to activated endothelial cells.

2. Description of the Prior Art

Septic shock is defined as a type of shock associated with overwhelming infection. Most commonly, the infection is produced by gram-negative bacteria although other bacteria, viruses, fungi and protozoa may also be causes. As summarized in Infectious Diseases and Medical Microbiology, 2nd edition, edited by Braude et al., Chapter 92, pages 700 et seq.

"Shock is a syndrome of generalized metabolic failure resulting from prolonged inadequacy of tissue perfusion. Its early clinical manifestations reflect malfunction of those organs most dependent on uninterrupted blood flow, particularly the brain, as well as compensatory adjustments designed to maintain adequate arterial pressure. As these adjustments fail, urinary output decreases and biochemical indices of distorted metabolism are detectable; specifically nonoxidative glycolysis with low yield of high energy chemical bonds testifies to the widespread nature of the disorder. In the end, it is the failure of energy production rather than damage to a particular organ that leads to death.

Other terms, such as 'circulatory collapse,' 'circulatory failure,' and 'hypoperfusion,' have been substituted for 'shock' in an attempt to pinpoint the specific nature of the derangement. When it occurs as a specific complication of infection, it is referred to as 'infectious shock,' 'septic shock,' 'bacteremic shock,' and even 'endotoxin shock.' The last three terms specifically implicate bacterial infection and are therefore too restrictive. Because 'infectious shock' is sufficiently broad as well as concise, this term will be used in the present chapter.

Shock may occur in the course of almost any severe infection, but it is particularly characteristic of bacteremia due to gram-negative bacilli. . . . The importance of endotoxin, the lipopolysaccharide (LPS) composing part of all gram-negative cell walls, is readily apparent because it produces a similar syndrome in experimental animals. Partly because of the extensive use of endotoxin as an investigative tool, endotoxin shock is commonly regarded as the prototype of infectious shock."

The shock is believed to be caused by the action of endotoxins, other products of the infectious agent, or host mediators released in response to the infectious agent on the vascular system. Such action causes altered patterns of perfusion of tissues and large volumes of blood to be sequestered in the capillaries and veins.

Sepsis, the sepsis syndrome, and septic shock are not discrete entities, but rather terms that delineate increasingly severe stages of the same disease. Septic shock, a frequently fatal reaction following bacterial infection, has been estimated to occur at a rate of 175 per 100,000 people yearly in the general population and rises to 500 per 100,000 for those people admitted to hospitals (Johnston, J. (1991) J. NIH 3: 61–65). Estimates range up to 400,000 cases of sepsis, 200,000 bouts of septic shock, and 100,000 deaths annually in the United States due to the septic shock induced syndrome (Snell, J. and J. E. Parrillo (1991) Chest 99: 1000–1009). Up to 40–50% of patients who develop septic shock die. The manifestation of septic shock involves a severe decrease in systemic vascular resistance and maldistribution of blood flow. Septicemia, a systemic disease associated with the presence and persistence of pathogenic microorganisms or their toxins in the blood, is currently ranked as the thirteenth leading cause of death in the United States (Annual Summary of Births, Marriages, Divorces, and Deaths: United States, 1988. Hyattsville, Md.: U.S. Department Health and Human Services, Public Health Service, CDC, 1989: 7. Monthly vital statistics report. 1989: 37[13]). Reasons underlying this high incidence of death from septic shock involve increased usage of cytotoxic and immunosuppressive drug therapies which impairs host defense mechanisms or increased use of invasive diagnostic devices or increased patient age (Snell, J. and J.E. Parrillo (1991) Chest 99: 1000–1009). Further causes of impaired host defense mechanisms include diabetes, malignant neoplasms, cirrhosis or extensive burns. The rising rate of infections from organisms other than gram-negative bacteria also contribute to the rise in septic shock induced death. Any bacteria can cause septic shock, however, the gram-negative bacteria (E. coli, Pseudomonas sp. and Bacteroides sp. ) in particular evoke septic shock due to the presence of lipopolysaccharide (LPS) in their cell walls. Bacterial LPS, also known as endotoxin, at concentrations as low as a few μ g/L can activate immune cells. The majority of damage induced from the presence of LPS is not due to the actual LPS itself, but is in fact a result of the body's complex reaction to the foreign LPS. This response is mediated by immune cell activation and the resultant damage that these activated cells cause to the host tissues.

Septicemia is difficult to reverse and the preferred treatment following the initial signs of hypoperfusion or shock include infusion of normal saline or lactated Ringer's solution. If shock persists then an aggressive fluid challenge is begun and the use of dopamine and/or norepinephrine is recommended. Cardiovascular insufficiency results from alterations to the myocardium and the vasculature and it is myocardial dysfunction that is responsible for hypotension or multiple organ system failure (Snell, J. and J. E. Parrillo (1991). Chest 99: 1000–1009). Unresponsive hypotension usually results from low systemic vascular resistance due to cardiovascular insufficiency which can not be corrected by any therapy. Multiple organ failure usually affects the lungs, kidneys, liver, heart, and central nervous system.

Treatment of septic shock is complex, requiring therapies directed at ameliorating the source of infection [antibiotics], blocking effects of products of the infectious agent and inflammatory mediators on tissues [anti-endotoxin (patent Young et al. U.S. Pat. No. 4,918,163) and anti-cytokine agents (patent Mandell et al. U.S. Pat. No. 4,965,271)], and maintenance of cardiovascular function [volume expansion and pressor agents]. However, mortality still runs at about 100,000 patients per year (40 to 50% of those in shock) and no therapies are available to prevent vascular contractile defects.

Other current approaches to the treatment of sepsis or septic shock involve neutralization of LPS with specific monoclonal antibodies, interference of cytokine-mediated immune responses, or inactivation of cell adhesion proteins with monoclonal antibodies. Targeting of LPS mediated sepsis, however, will be effective only against gram-negative bacteria since LPS is only found in their cell walls. Monoclonal antibodies to the lipid A domain of LPS have had some success at intervention with LPS mediated septic shock from gram-negative bacteria, but not for non-gram-negative induced septic shock (Ziegler, E.J et al. (1991) N. Eng. J. Med. 324: 429–436). Thus, while the gram-negative LPS may be the most potent inducer of sepsis, gram-positive bacterial infections occur in 60–70% of all cases. Intervention with cytokine mediated activation of the immune response as a means of preventing septic shock would not only interfere with gram-negative induced sepsis, but also shock caused by gram-positive bacterial infection or other agents. The development of an effective therapy to treat all bacterial induced septic shock would be of obvious benefit to patients who are at an increased risk of bacterial induced sepsis and provide increased survival from septic shock and the complications that arise during septic shock induced dysfunctions. Another approach would be interference with the cellular response to the various endogenous mediators (cytokines, PAF, arachidonic acid metabolites, histamine, endorphins, etc) responsible for vasculature effects. These approaches are not currently approved for therapy and are in clinical trials.

One of the major effects experienced by the vasculature is destruction of endothelial cells by leukocytes. Inflammation is characterized by the local accumulation of leukocytes, plasma proteins, and fluid usually at an extravascular site. Inflammatory processes are intrinsically destructive to the surrounding tissues and may, in certain circumstances such as allograft rejection or sepsis, be more harmful than beneficial. Thus, an appropriate strategy for the treatment or prevention of sepsis or septic shock would be down-regulation, but not total ablation, of the inflammatory response. Down-regulation of specific cell adhesion receptors and/or ligands to the receptors would be one approach to preventing, or lessening, the inflammatory mediated damage to endothelial cells in the vasculature.

The involvement of the immune response in the development of septic shock and its lethal consequences provides a target that is applicable to the use of antisense oligonucleotides. Antisense oligonucleotides can be used to inhibit expression of the key receptors and cellular ligands involved in the activation of the immune response. The migration of leukocytes into tissues is the central event in the immune or inflammation response. This migration to and subsequent emigration into the tissue is responsible for the successful host response to injury and infection. The leukocytes are also potentially harmful and contribute to the pathology of many inflammatory disorders. The precise mechanism of this injury is not known, but the generation of free oxygen radicals and release of proteolytic enzymes have been implicated and may act together in leukocyte induced endothelial cell damage (Varani, J. et al. (1989), Am. J. Path. 135: 429–436). Evidence for the leukocyte adhesion to endothelial cells has been attributed to specific surface proteins. Involved in the binding of leukocytes to activated endothelium is a family of endothelial cell adhesion molecules known as the selectins or LECCAMs. One member of this family is the endothelial leukocyte adhesion molecule-1, also known as ELAM-1. ELAM-1 is a 110 kD cell-surface glycoprotein of endothelial cells that binds neutrophils and perhaps monocytes (Bevilacqua, M.P et al. (1987) Proc. Natl. Acad. Sci. USA 84: 9238–9242). There are two pathways for the adhesion of leukocytes to endothelium: 1 ) an immediate adhesion that is not dependent upon the de novo synthesis of proteins, and 2) a delayed adhesion (1–2 hours) that is dependent upon the synthesis of proteins (Osborn, L. (1990) Cell 62: 3–6). The synthesis and surface presentation of ELAM-1 in endothelial cells suggests that ELAM-1 may be involved in the second, or delayed, component of leukocyte adhesion (Bevilacqua, J.S. et al. (1987) Proc. Natl. Acad. Sci. USA 84:9238–9242 and Bevilacqua, J.S. et al. (1989) Science 243: 1160–1165). Endotoxin or LPS can increase the adhesion of leukocytes to endothelial cells through the biosynthesis and expression of ELAM-1. Stimulation of human umbilical vein endothelial cells (HUVECs) with either interleukin-1 or tumor necrosis factor-alpha results in more than a 100-fold increase in the surface presentation of ELAM-1 (Osborn, L. et al. (1990) Cell 62: 3–6). Also, the stimulation of ELAM-1 synthesis and its presentation on the surface of HUVECs has shown to be mediated with endotoxin (Munro, J.M. et al. (1991) Lab. Invest. 64: 295–299). Injection of endotoxin into the skin of baboons results in the strong, widespread endothelial binding of anti-ELAM-1 antibodies in the venules by 2 hours after the injection. This two hour delay in presentation of ELAM-1 to the venules correlated with the time course for adherence of neutrophils. After 9 hours the expression of ELAM-1 and the ability of ELAM-1 to be recognized by the antibodies had declined to pre-injection levels (Munro, J.M. et al. IBID). Thus, this study demonstrates that the early dermal accumulation of neutrophils after injection of endotoxin is associated with the endothelial cell expression of ELAM-1. These in vivo effects closely parallel the in vitro evidence concerning the induction of ELAM-1 by endotoxin and the role of ELAM-1 in neutrophil adhesion. The ability of antibodies to ELAM-1 to block the adhesion of neutrophils, eosinophils, and basophils induced in vitro in HUVECs by interleukin-1 suggests that ELAM-1 plays an important role in the requirement of these cells during the inflammatory response (Bochner, B.S. et al. (1991) J. Exp. Med. 173:1553–1556 and Carlos, T. et al. (1991) Blood 77: 2266–2271).

Leukocytes, especially neutrophils, may injure endothelial cells (Pober, J.S. and Cotran, R.S. (1990) Transplant. 50: 537–544). While the exact mechanism is not known, the damage may be induced by oxygen radicals or proteolytic enzymes released from the neutrophils. Damage to the endothelial cells lining the vasculature results in leakage into the surrounding tissues. The pulmonary leak that is produced in adult respiratory distress syndrome, a resultant complication of septic shock, most often results from neutrophil-mediated capillary injury (Helfin, A.C. and K.L. Brigham (1981) J. Clin. Inv. 68: 1253–1260).

ELAM-1 eDNA and the genomic clones have been isolated and the nucleic acid sequence of the pre- and mature-mRNA can be determined from these sequences (Goelz, S.E et al. (1990) Cell 63: 1349–1355; Hession, C. et al. (1990) Proc. Natl. Acad. Sci. USA 87: 1673–1677; and Collins, T. et al. (1991) J. Biol. Chem. 266: 2466–2473). Thus, the ability to target the pre- or mature-mRNA with antisense oligonucleotides with the express purpose of down-regulating the synthesis of ELAM-1 is immediately possible.

Involved in the activation of the inflammatory and immune response, as during the development of sepsis and septic shock, is the expression of many essential cell adhesion proteins and receptors. Adhesion molecules are activated by various cellular mediators, exogenous or endogenous to the host, and therefore, the logical approach is down-regulation of adhesion protein expression as opposed to treatments aimed at the multiple activators. Thus, the use of antisense oligonucleotides to specifically down-regulate adhesion protein expression would be of obvious advantage to most therapeutic approaches to septic shock.

Research by others into PKC inhibition and treatment of inflammatory responses have disclosed that endothelial cells express adhesive proteins in response to sepsis associated stimuli such as endotoxin or cytokines, such as interleukin-1 (IL-1) and Tumor Necrosis Factor (TNF). Magnuson, D.K. et aL ((1989) Surgery 106: 216–223) and Lane, T.A. et al. ((1990) Biophys. Res. Comm. 172: 1273–1281) have shown that these adhesive proteins can be reduced on endothelial cell surfaces by inhibition of PKC with staurosporine or 1-(5-isoquinolinylsulfonyl)-2-methyl piperazine (H7). Surface presentation of these adhesive proteins enhances white blood cell infiltration and activation which can result in tissue damage in inflammatory states like septic shock. In addition, PKC activation enhances endothelial cell permeability resulting in edema. This response to inflammatory agents was also abrogated by exposure of the cells to the PKC inhibitor H7 (Lynch, J.J. et al. (1990) J. Clin. Invest: 85:1991–1998). Abnormal leukocyte accumulation is implicated in a variety of inflammatory states such as: reperfusion injury, autoimmune diseases, and acute respiratory distress syndrome (ARDS). The damage is thought to result from the release of toxic oxygen radicals and proteases that potentiate tissue damage. The use of anti-adhesive protein antibodies or adhesive like proteins was shown to reduce tissue damage in select models of reperfusion injury (Vedder, N.B. et al. (1988), J. Clin. Inv. 81: 939–944; P.J. Simpson et al. (1988) J. Clin. Inv. 81: 624–629; M. J. Horgan et al. (1989) Am. J. Physiol. 259: L315–319; International Patent Application of inventors Vadas, M, and M. Berndt (1991) Application #WO 91/07993) and endotoxin induced damage (H. Rosen and S. Gordon (1989) Br. J. Exp. Path 70: 385–394). When antibodies are used as a treatment they do not control the levels of expression of these proteins and the antibodies typically have short half-lives in circulation. An additional complication of antibodies is the potential for immunogenic reactions to large foreign proteins. Compared to antibodies, smaller molecules like antisense oligonucleotides can overcome these disadvantages and also provide selective control of expression of a single cellular protein.

The mRNA coding for ELAM-1 has been cloned and the nucleic acid sequence is available for selective targeting with antisense oligonucleotides (Collins, T. et al. (1991) J. Biol. Chem. 266: 2466–2473).

Antisense Background

The use of antisense oligonucleotides for therapeutic purposes was first proposed in 1978 by Stephenson, M.E. and P.C. Zamecnik ((1978) PNAS 75: 285–288). The concept behind antisense therapy relies on the ability of antisense oligonucleotides to be taken up by cells and form a stable heteroduplex with the target mRNA. The end result of antisense oligonucleotide hybridization is the down regulation of the targeted protein's synthesis. Down regulation of protein synthesis by antisense oligonucleotides has been postulated to result from two possible mechanisms: 1) "hybrid arrest", where direct blocking in pre-mRNA and/or mRNA of sequences important for processing or translation prevents full-length proteins from being synthesized; and 2) an RNase H mediated cleavage and subsequent degradation of the RNA portion of the RNA:DNA heteroduplex (Haeuptle, M. et al. (1986) Nuc. Acids Res. 14: 1427–1448; Minshull, J. and J. Hunt (1986) Nuc. Acids Res. 14: 6433–6451). Thus, the use of antisense oligonucleotides could down-regulate the expression of proteins or enzymes that are implicated in the etiology of a disease state. Down regulation of a protein is functionally equivalent to a decrease in its activity, the mechanism of action of most traditional pharmaceutical drugs.

The interaction of the antisense oligonucleotide with the target mRNA is highly specific as hybridization is determined by the sequence of bases complementary to the antisense oligonucleotide, or by the Watson/Crick base pairing of the two strands of nucleic acid. Thus, there are multiple points of contact between the antisense oligonucleotide and the mRNA target, which increases the specificity for hybridization to the correct sequence. This specificity derived from the Watson/Crick base pairing is not evident in traditional drugs that inhibit the activity of proteins or mimick their action. Potential side effects experienced with traditional drug therapies results through interactions at a few contact points between the drug and various proteins that possess similar binding sites or sites of interaction. Such adverse effects should be eliminated with antisense drugs. Experimental calculations using the number of base pairs in the human genome and the frequency of base utilization predict that there would be a single complement to a 14-mer antisense oligonucleotide in the entire human genome (Ts'o, P.O.P. et al. (1987) Biological Approaches to the Controlled Delivery of drugs, Vol 507, Ann. N.Y. Acad. Sci.). This level of specificity is not achievable with traditional drugs.

Evidence for down regulation of protein synthesis by antisense oligonucleotides has been well documented in vitro (for reviews see van der Krol, A.R. et al. (1988) BioTechniques 6: 958–976; Cohen, J.S. (1991) Antiviral. Res. 16: 121–133). In vivo studies using antisense oligonucleotides have demonstrated that injection of radiolabeled antisense oligonucleotides into the blood of mice results in distribution of full-length labeled oligonucleotide to the various tissues. Once in the tissue, oligonucleotides can elicit an antisense effect by binding to the correct mRNA and, thus, be suitable for a therapeutic approach to a disease state (Miller, P.S. and P.O.P Ts'o (1987) Anticancer Drug Design 2: 117–128). Recently, antisense oligonucleotides have been shown to elicit a reduction in myc gene expression using an in vivo mouse model for B-cell lymphoma myc expression (Wickstrom, E. et al. (1991) FASEB J. 5: A1442). Other in vivo data has shown that antisense oligonucleotides to 5' viral sequences of tick-borne encephalitis virus were capable of providing protection (30–50% survival in treated animals versus 100% lethality for control mice receiving no antisense oligonucleotide) in mice from viral induced death (Pogodina, V.V., et al. (1989) Dokl-Akad-Nauk-SSSR 308: 237–240). Further evidence for in vivo efficiency of antisense oligonucleotides in mice has shown that subcutaneous injection of a phosphorothioate oligonucleotide could inhibit the synthesis of interleukin-1 receptor protein (Burch, R. and L.C. Mahan (1991) J. Clin. Invest. 88: 1190–1196). The infiltration of neutrophils into the dermal injection site of IL-1 was used as a means of assessing the ability of injected antisense oligonucleotides to inhibit IL-1 receptor synthesis. It was shown that three, 3 nmole, subcutaneous injections of phosphorothioate anti-IL-1 receptor oligonucleotides (24 hr intervals) significantly reduced neutrophil infiltration. Control injections of saline or mismatch containing oligonucleotides did not inhibit neutrophil infiltration. Thus, antisense oligonucleotides targeted to the IL-1 mRNA were able to prevent IL-1 induced neutrophil infiltration in mice.

The stability, pharmacokinetics, and bio-distribution of antisense oligonucleotides in vivo have also been reported in mice. Using phosphorothioate antisense oligonucleotides, about 30% of either i.p. or i.v. injected oligonucleotide was retained in the animal with the remaining oligonucleotide being excreted in the urine (Agrawal, S. et al. PNAS 88: 7595–7599, 1991). The oligonucleotide retained within the animal was found within most tissues up to 48 hours. There were differences in the rates of degradation within the various tissues, with the plasma, stomach, heart and intestine showing the most intact oligonucleotide (15% degraded). In the kidney and liver degradation was 50% or greater after 48 hours. All of these experiments demonstrate that the antisense oligonucleotides are capable of reaching tissues in vivo and that the expression of gene products, proteins derived from mRNA translation, can be specifically down-regulated by antisense oligonucleotides in live animals.

A major issue to be addressed in the use of antisense oligonucleotides for in vivo treatment is the stability of the molecule to the action of nucleases. Use of unmodified oligonucleotides containing phosphodiester linkages has not proven valuable in antisense therapy since these oligonucleotides are susceptible to exo- and endonucleases present in serum and cells. Thus, modifications of the natural, or phosphodiester deoxyoligonucleotides (PO-ODN) have been developed that provide increased stability to degradation (for review Uhlmann, E. and A. Peyman (1990) Chemical Reviews 90: 543–584). One of these modifications is the replacement of one of the non-bridging oxygen atoms in the phosphodiester linkage with sulfur to produce a phosphorothioate deoxyoligonucleotide (PS-ODN). The introduction of sulfur atoms in the PS-ODNs do not disrupt hybridization significantly compared to unmodified PO-ODNs, retains the relative solubility of PO-ODNs in aqueous media and provides significantly enhanced resistance to serum and cellular nucleases (Stein, C.A. et al. (1988) Nuc. Acids Res. 16: 3209–3221: Campbell, J.M. (1990) J. Biochem. Biophys. Methods 20: 259–267). Other modifications include methylphosphonates, phosphorodithioate, sugar modifications, and heterocycle modifications (Goodchild, J. (1990)Bioconjugate Chem 1: 165–186). Of various modifications to oligonucleotides, the PS-ODNs are suitable for antisense approaches to in vivo therapy at the present time, however, as novel chemistries become available there may be many new chemical modifications of antisense oligonucleotides that have increased potential for therapeutic applications.

The bio-availability of antisense oligonucleotides to target cells is another important issue that arises in the use of oligonucleotides for therapy. Enhanced cellular uptake has been reported using a wide variety of techniques including LIPOFECTIN™ (Life Technologies, Gaithersburg, Md.) (Chiang, M-Y. et al. (1991) J. Biol. Chem. 266: 18162–18171), lipoproteins (de Schmidt, P.C. (1991) Nuc. Acids Res. 19: 4695–4700), and a wide variety of conjugates, including poly-L-lysine or cholesterol etc (for review see Goodchild, J. (1990) Bioconjugate Chem. 1: 165–186). The ability to increase the uptake of ODNs into cells will become more diverse as more data accumulates. Conjugation of cholesterol to the 5' end of an oligonucleotide resulted in a molecule that exhibited reduced serum clearance, due to reduced kidney excretion, compared to control ODNs (de Smidt, P.C. et al. (1991) Nuc. Acids Res. 19: 4695–4700). This conjugation of cholesterol to ODNs may result in increased delivery to liver cells via the LDL transport mechanism. Other possibilities for increasing cellular uptake include modulation of the 80 kDa surface protein putatively involved in transport of oligonucleotides into cells. The availability of more information on this protein may provide insight into certain modifications that increase the activity of the transporter (Loke, S.L., et al. (1989) Proc. Natl. Acad. Sci. USA 86: 3472–3478). The conjugation of ODNs to certain biological molecules that are taken up into cells by specific receptors may provide an in vivo advantage in antisense oligonucleotide delivery. For example, conjugation of folate to the oligonucleotide may provide a selective cellular uptake mechanism through the endocytosis mediated vitamin folate pathway (Leamon, C.P. and P.S. Low (1991) Proc. Nat. Acad. Sci. USA 88: 5572–5576). Conjugation of folate to antibodies has demonstrated that this approach with large macromolecules is feasible. Thus, conjugations, such as folate or other ligands recognized by receptors, or to agents that carry the ODNs into cells via endocytotic uptake pathways, may be an extremely useful approach to antisense therapy. There may also be other conjugations that would target oligonucleotides to specific cells or organs which would decrease the effective concentration of oligonucleotide needed in a specific therapy. However, present data suggests that antisense oligonucleotides with modifications like phosphorothioate or methyl phosphonate are capable of tissue distribution and cellular uptake. Thus, at the present time an oligonucleotide sufficiently stable to nuclease degradation should be distributed to the cells and undergo cellular uptake.

Recently, it has been reported that antisense PS-ODNs are capable of down-regulating the in vitro expression of one member of the immunoglobin superfamily adhesion proteins involved in cell-cell adhesion, ICAM-1 (Chiang, M-Y. et al. (1991) J. Biol. Chem. 266: 18162–18171). These data suggest that antisense oligonucleotides, particularly those stable to nucleases, like the phosphorothioate or 2'-O-methyl modified antisense oligonucleotides, are capable of inhibiting the expression of cell adhesion molecules. Thus, the use of antisense oligonucleotides in the down-regulation of ICAM-1 and other adhesion molecules should provide a basis for therapy and treatment of inflammatory disorders, particularly septic shock. Inhibition of the inflammatory response component of sepsis may provide the necessary protection to prevent the lethal consequences of septic shock brought about by the body's own immune system.

While there are several generalized locations within the linear nucleotide sequence of any mRNA that may provide an increased capacity for antisense oligonucleotide intervention with the flow of information from the gene to the protein product, there is, as of yet, no way to predict the optimum sequence for an active antisense oligonucleotide. Uhlman and Peyman (1990) discuss the potential mechanisms of action for antisense oligonucleotides as inhibition of splicing, polyadenylation, translocation, translation and ribosome movement along the mRNA but the actual selection of a particular sequence is only discussed in general terms. One would select antisense oligonucleotides that target nucleotide sequences anywhere in a particular mRNA (i.e. 5'-untranslated region, coding region, 3'-untranslated region, or combinations thereof) because one wants to inhibit the expression of that mRNAs protein. One would not want to select an antisense sequence that is complementary to one protein's mRNA when the objective is to inhibit the expression of another protein. However, the selection of an antisense sequence, anywhere (whether located in the 5'-untranslated region, coding region, 3'-untranslated region, or combinations thereof) within the nucleotide sequence of the target protein's mRNA will not always produce active antisense compounds.

Recent literature shows a number of specific examples of very potent in vivo therapeutic efficacy for antisense oligonucleotides. The examples cited below show three different therapeutic targets that indicate the wide range of therapeutic activity for antisense oligonucleotides.

The first study (Simons, M. et al., 1992, Nature 359:67–70) shows that an antisense phosphorothioate directed against c-myb can be delivered in vivo to rat carotid arteries stripped of their intima. The oligonucleotides were formulated in a pluronic gel containing 200 micrograms of drug and applied to the outer layer of the arteries. The drug had to reach the smooth muscle cells surrounding the intimal layer, in order to have a therapeutic effect. Indeed, the antisense oligonucleotide effectively prevented restenosis or regrowth of smooth muscle cells around the stripped regions. This effect indicates strongly that antisense can be therapeutically effective in living rats in a stringent model.

A second study shows that a human leukemia can be treated successively in a scid mouse model with antisense oligonucleotides against c-myb (Ratajczak, M.Z. et al., 1992, Proc. Natl. Acad. Sci. USA 89:11823–11827). This work established human leukemia-scid mouse chimeras with K562 cells and treated diseased animals with phosphorotioate-modified antisense oligonucleotides against c-myb. The results showed that control oligonucleotides had no effect on survival, whereas animals treated with antisense constructs survived at least 3.5 times longer than the various control animals. Antisense treated animals had significantly less disease at sites where leukemia is often refractory to treatment, the brain and the ovary. The drug was delivered to the animals by Alzet minipumps that released 1.0 microliter per hour into a paraspinal pocket at a 100 microgram per day so that each animal received 5 mg/kg or 1.0 micromolar dose. Thus, based on the results of this animal model, it seems quite reasonable that antisense may have efficacy in this and other cancer models.

A third study shows that antisense oligonucleotides to the NMDA-R1 receptor channel can protect cortical neurons of rats from excitotoxicity and reduce focal ischemic infarctions (Wahlestedt, C. et aL, 1993, Nature 363:260–263). In this rat model of stroke, antisense therapy was more effective than MK-801, the most effective small molecule therapy for stroke. The antisense drug was delivered intraventricularly in a dose of 15 nmol in 5 ul $H_2O$. The appropriate controls had no effects.

In summary, these data show that antisense therapy applied to stringent animal models of human disease can cause profound therapeutic benefits in the models. One can thus say that, while there is more in vitro antisense data, the efficacy seen in these animal models is sufficient to predict that there may be profound therapeutic benefit in humans from antisense drugs discovered in vitro. Of course this is precisely the situation for standard small molecule drugs discovered in vitro.

Investigations into the toxicity of antisense oligonucleotides has not revealed significant damage or lethality to cells. In vitro studies into the toxicity of antisense oligonucleotides has been limited primarily to modified oligomers where the phosphodiester linkages between the sugar moieties has been replaced with either phosphorothioates or methylphosphonates. Generally, phosphorothioates are nontoxic in a variety of cell lines (for example, Reed, J.C. et aL (1990) Cancer Res. 50: 6565–6570).

SUMMARY OF THE INVENTION

Accordingly, an object of the invention is a therapy to lessen morbidity and mortality caused by septic shock and the ensuing complications and associated symptoms.

An additional object of this invention is a method of treating the symptoms of septic shock.

Yet another object of this invention are agents to prevent vascular and tissue defects associated with manifestations of septic shock.

Another object of this invention is a formulation of an inhibitor of the inflammatory response that is a major cause of the complications resulting in septic shock.

An additional object of this invention is a method for inhibiting the adhesion of leukocytes to the endothelium of the vasculature, where the adhesion of leukocytes to the endothelium is the initial event in the development of the inflammatory response.

The foregoing objects of the present invention are accomplished by providing an improved therapeutic treatment for the collective diseases of 'sepsis' that result from inflammatory response mediated changes in the vasculature by using nucleic acids, either as oligonucleotides or polynucleotides, as antisense inhibitors of protein translation, specifically ELAM-1.

These and additional objects of the invention are accomplished by treating the subject susceptible to septic shock with antisense oligonucleotide, preferably with a sequence which inhibits synthesis of the protein ELAM-1. Preferred are those oligonucleotides which substantially form a stable hybrid with at least a portion of the gene or mRNA coding for ELAM-1. Preferred is an oligonucleotide that comprises a sequence that forms a stable hybrid with at least a portion of the 5' UTR (UnTranslated Region), translation initiation codon, coding region, or 3' UTR of the pre- or mature- mRNA for ELAM-1. Other preferred sites include the remaining regions of the exons of the gene and the intron regions to inhibit pre-mRNA processing. The inhibitors of this invention are administered, preferably by intravenous infusion in a suitable pharmaceutical carrier, in a range of 0.01 to 500 mg/Kg body weight preferably in the range of 0.05 to 250 mg/Kg body weight and most preferably in the range of 0.15 to 50 mg/Kg body weight.

In preferred embodiments, these antisense oligonucleotides comprise a nucleotide sequence that forms heteroduplexes within the 5' untranslated region of the mRNA, the translational initiation codon, the sequence immediately downstream from the translation initiation codon, unique portions of the 3' untranslated regions, or combinations thereof. These oligonucleotides may comprise from a 10- to a 30-mer (bases) selected from the group consisting of the oligonucleotides GTF TAA GGC AGC ATC CTA AGA (SEQ ID No. 1); TCA CCC AAA GGT TTA GGC TFG (SEQ ID No. 2); GCA ATC ATG ACT TCA AGA GTF (SEQ ID No. 3); GTT CAC AAC TGA AAA ACA AAC (SEQ ID No. 4); GCA TGT CAC AGC TGT AAC AAA (SEQ ID No. 5); TGA AGT CAG CCA AGA ACA GCT (SEO ID No. 6); CGT TCT GCA CTT ACC GTr TTG (SEQ) ID No. 7); GAA ATA CTT TCC TGG GGA GAT (SEQ ID No. 8); CAG CCA AGA ACA GCT (SEQ ID No. 9); CAG CCA AGA ACA GCT GG (SEQ ID No. 10); GAT GTG AAG TCA GCC AA (SEO ID No. 11); CCC AAA GGT TTA GGC TFG (SEQ ID No. 12; and GAG TTC TTT TCA CCC (SEQ ID No. 13) wherein the sequences as listed are in the 5' to 3' direction.

The oligonucleotide can be used to inhibit the expression of the human ELAM-1. Thus, the invention encompasses the use of at least one oligonucleotide, alone or in combination in the therapeutic treatment of patients suffering from septic shock or the resultant complications from sepsis.

In a preferred embodiment of the invention, a therapeutically effective concentration of oligonucleotide can be administered to a patient so as to substantially block the translation of the human ELAM-1 mRNA, thereby substantially reducing the complications of sepsis.

The present invention also provides a pharmaceutical composition comprising one or more oligonucleotides of the invention in combination with a suitable pharmaceutical carrier according to conventional pharmaceutical techniques.

BRIEF DESCRIPTION OF THE DRAWINGS

A more complete appreciation of the invention will be readily obtained by reference to the following Description of the Preferred Embodiments and the accompaning drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
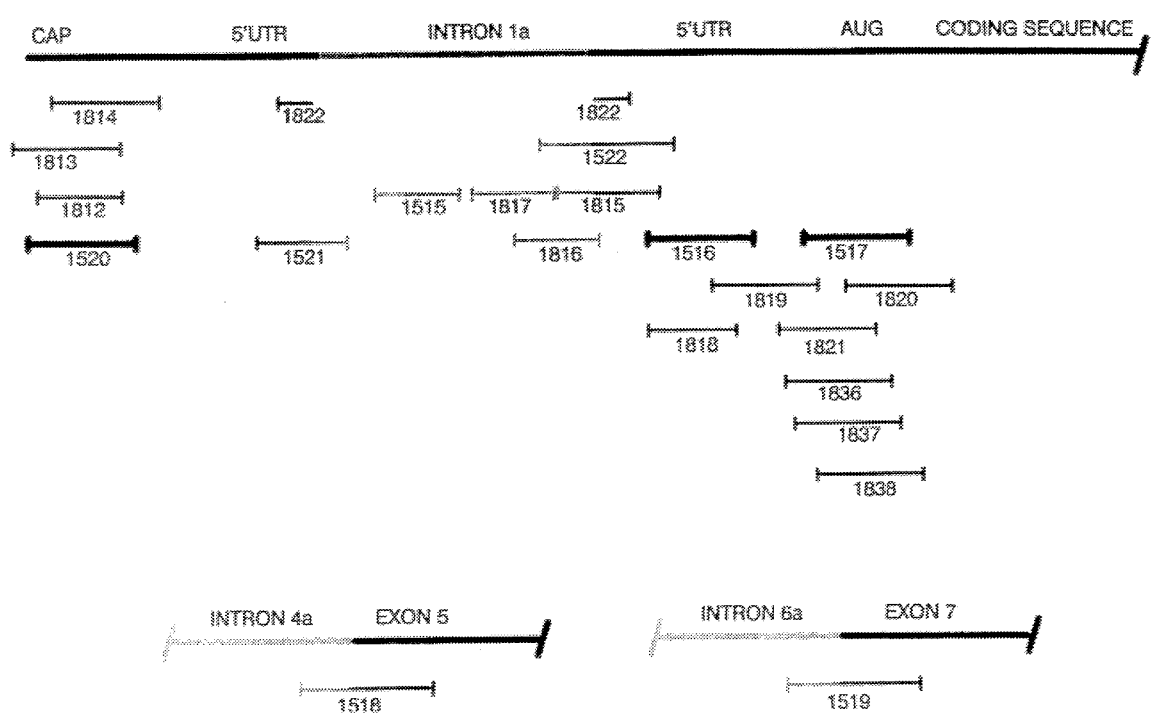
FIG. 1 is a map of the ELAM-1 pre-mRNA showing oligonucleotides that are part of this invention.

In accordance with the detailed description, the following definitions apply:

Antisense oligonucleotides—any natural or modified oligonucleotide or chemical entity that binds specifically to a pre-mRNA or mature mRNA which results in interference or inhibition with translation of the mature mRNA or prevents the synthesis of the polypeptide encoded by the mature mRNA.

Septic shock—septic shock is used in this invention to convey any of the various states of the collective diseases known as sepsis, sepsis syndrome, septic shock, incipient septic shock, bacteremia, refractory septic shock, or any of the diseases associated with sepsis such as ARDS (adult respiratory distress syndrome), multiple organ failure, cardiac dysfunction, etc.

ELAM-1—ELAM-1 in this invention describes the Endothelial Leukocyte Adhesion Molecule-1 involved in adherence of leukocytes (monocytes and neutrophils especially).

mRNA—mRNA refers to mature, processed mRNA or unprocessed, nuclear pre-mRNA (ribonucleic acid) to the ribonucleic acid transcribed from the gene(s) encoding for the synthesis of ELAM-1. These sequences of ribonucleic acid are used to select the antisense oligonucleotide sequences which are complementary to discrete portions of the mRNA or pre-mRNA.

As used herein, unless otherwise indicated, the term "oligonucleotide" includes both oligomers of ribonucleotides i.e. oligoribonucleotides, and oligomers of deoxyribonucleotides i.e. oligodeoxyribonucleotides, or oligodeoxynucleotides.

Unless otherwise indicated, the term "oligonucleotide" also includes oligomers which may be large enough to be termed "polynucleotides".

The terms "oligonucleotide" and "oligodeoxynucleotide" include oligomers and polymers of biologically significant nucleotides, adenine, deoxyadenine, guanine, deoxyguanine, thymine, uracil, cytosine and deoxycytosine, as well as oligomers and polymers which contain other novel nucleotides and are hybridizable to the target mRNA transcript. These terms also include oligomers and polymers having one or more purine or pyrimidine moieties, sugar moieties, or internucleotide linkage(s) which has or have been chemically modified. Such modifications may be substantial and may encompass nonnucleotide chemistries including non-sugar, non-phosphate backbone, and chemical alterations to the bases to maintain the specific hybridization to the mRNA by base-pairing mechanisms, similar to or different from Watson-Crick base pairing. These terms further include those oligomers or polymers that are composed of nucleoside containing bases joined to the sugar moieties in the alpha configuration.

The term "downstream" is used herein to indicate the 5' to 3' direction in a nucleotide sequence. Similarly, the term "upstream" indicates the 3' to 5' direction.

The term "complementary" is used herein to indicate that the oligonucleotide is capable of hybridizing to and forming a duplex with its target sequence in the mRNA transcript.

The term "stable duplex" or a "stable hybrid" is used herein to indicate that 50% or greater of the oligonucleotide is bound in said duplex with its target sequence in the mRNA transcript at a temperature of 40° C. in 10 mM sodium phosphate, lmM ethylenediamine tetraacetic acid and 128 mM sodium chloride, pH 7.

The term "mRNA" is used herein to indicate either the mature or processed mRNA, or the unprocessed nuclear pre-mRNA.

According to a preferred embodiment of the present invention, antisense oligonucleotides are synthesized using standard published techniques for the synthesis of phosphorothioate, PS, oligonucleotides, ODNs. Synthesis of antisense oligonucleotides is performed using a solid support and a commercially available DNA synthesizer. Antisense oligonucleotides are synthesized using standard phosphoramidate chemistry. For phosphodiester linkages the oxidation is mediated via iodine, while for the synthesis of phosphorthioates, the oxidation is mediated with a 0.2M solution of 3H-1,2-benzodithiole-3-one,1,-dioxide in acetonitrile (Iyer, R.P., et al. (1990) J. Amer. Chem. Soc. 112:1253–1254) for the step-wise thioation of the phosphite linkages. The thioation step is increased to 68 sec and is followed by a capping step. Following synthesis and cleavage from the control pore glass support, the trityl-on oligonucleotide is purified using HPLC. HPLC methodologies consist of chromatography using an PRP-1 column and gradient of acetonitrile in 50 mM triethylammonium acetate, pH 7.0 (4–32% in 30min, flow rate of 1.5 ml/min). Appropriate fractions are pooled, evaporated, treated with 5% acetic acid for 15 min at ambient temperature. The oligonucleotide solution is extracted with an equal volume of ethyl acetate, neutralized with ammonium hydroxide, frozen and lyophilized. Solution based chemistries are also useful for synthesis of antisense oligonucleotides and are useful for scaled-up synthesis of oligonucleotides.

DETAILED DESCRIPTION OF THE INVENTION

The present invention is concerned with oligonucleotides having therapeutic value, therapeutic compositions containing these oligonucleotides and methods for use thereof. The present invention is the result of research on septic shock and the role of inflammation in the resultant morbidity or mortality resulting from septic shock. Accumulated information has led to the conclusion that disruption of the inflammatory response would be a method of choice in the treatment of septic shock and the resulting complications.

It has previously been demonstrated in a number of systems by various investigators that oligonucleotides complementary in sequence to a portion of a particular mRNA are capable of hybridizing to the mRNA and inhibiting the translation of the transcript.

In accordance with the present invention, an oligonucleotide having a base sequence capable of hybridizing to the mRNA transcript of the human ELAM-1 adhesion receptor is provided. Hybridization of the oligonucleotide to the ELAM-1 mRNA substantially blocks the translation of the mRNA transcript. Because ELAM-1 is essential for the initial attachment or adhesion of leukocytes arising from stimulations that induce septic shock, down-regulation of ELAM-1 would provide a benefit to the patient in the form of a reduced inflammatory response.

The oligonucleotides of the present invention are constructed and purified methods known in the art. The specific oligonucleotide sequence is complementary to a portion of ELAM-1 mRNA or gene. In particular, the oligonucleotide sequence is complementary to a portion of ELAM-1 transcript, such as the portion of the transcript including the translation initiation codon, and sequences 5' and/or 3' to the translation initiation site, of the 5' cap region of the mRNA and sequences 3' to the cap site. Another oligonucleotide sequence is also made complementary to a sequence contained in the 3' untranslated region of the ELAM-1 gene that is substantially unique to the ELAM-1 gene. Moreover, antisense oligonuculeotides that are capable of cross-linking DNA or intercalating DNA can be made complementary to any portion of the ELAM-1 gene. Furthermore, the invention contemplates that any oligonucleotide capable of specifically and substantially inhibiting the expression of ELAM-1 can be used.

The oligonucleotide's of this invention comprise predetermined sequences of DNA ranging in size from about 10 bases up to about 30 bases, which is sufficient to define a unique sequence in the human ELAM-1 target mRNA transcript. Less than 14 bases may be used, however the degree of sequence uniqueness decreases rapidly with decreasing length and thereby greatly reducing the specificity of the oligonucleotide for the ELAM-1 mRNA transcript. On the other hand, oligonucleotide sequences greater than about 30 bases may be subject to decreased cellular uptake and have an increased likelihood of containing short stretches of nucleotide sequence that is capable of forming quasi-stable hybrids with non-target mRNA sequences, other than the ELAM-1 mRNA transcript. It is preferable that the oligonucleotides comprise about 15 to 25 bases. In the most preferred embodiment of this invention, a 21-mer oligonucleotide is used selected from the group consisting of GTF TAA GGC AGC ATC CTA AGA (SEO ID No. 1); TCA CCC AAA GGT TTA GGC TTG (SEO ID No. 23.; GCA ATC ATG ACT TCA AGA GTT (SEQ ID No. 3); GTT CAC AAC TGA AAA ACA AAC (SEQ ID No. 4); GCA TGT CAC AGC TGT AAC AAA (SEQ ID No. 5); TGA AGT CAG CCA AGA ACA GCT (SEQ ID No. 6); CGT TCT GCA CTT ACC GTT TTG (SEQ ID No. 7); and GAA ATA CTT TCC TGG GGA GAT (SEQ ID No. 8).

The oligonucleotide sequence may be prepared by solid phase or solution phase synthesis in an automated nucleic acid synthesizer or via solution phase techniques. Also, in a less preferred method, the oligonucleotide may be prepared through the use of reverse transcriptase, PCR synthesis, or via other genetic engineering techniques. The method of preference for this invention is synthesis of the oligonucleotide using automated DNA synthesis on a solid phase support. Any means of synthesis of the oligonucleotides is within the scope of this invention.

Modifications to the oligonucleotides may be used to increase several desirable properties, including solubility, enhanced uptake, or enhanced stability to degradation, for example. Thus, modifications to the phosphate backbone, termini, sugar moiety, or the individual nucleic acid bases are within the scope of this invention. A preferred modification to the oligonucleotides is the alteration of the phosphodiester linkage between the sugar moieties. A more preferred embodiment of this invention is the use of phosphorothioate linkages between the sugar moieties. The combination of various modifications, for example, phosphate backbone modifications in combination with any number of terminal conjugates, is within the scope of this invention. The terminal modifications may include cross-linking agents, intercalators, photochemically activated moieties, alkylating agents and redox active nucleic acid cleavage groups. Also included are modifications that are nonnucleotide based in chemistry but that still form stable heteroduplexes with at least a portion of the ELAM-1 mRNA. For example, non-nucleotide i.e. $(CH_2)_n$ linkers between oligonucleotides are included.

The composition of the present invention comprises at least one oligonucleotide having a nucleotide sequence at least substantially complementary to at least a portion of the human ELAM-1 mRNA transcript in a suitable pharmaceutical carrier. The amount of oligonucleotide in the composition can range from about 0.01% to 99% by weight of the composition. The oligonucleotide can be mixed with a variety of carrier compounds depending upon the form of the preparation desired for administration, e.g. delivery by i.v modalities. The more preferred means of delivery is via an i.v. solution prepared with any of the usual pharmaceutical components.

The selection of antisense oligonucleotides that exhibit activity against a particular mRNA requires the determination of active antisense oligonucleotides experimentally. For example, data obtained from evaluating the capacity for a series of antisense oligonucleotides targeting the mRNA for Endothelial Leukocyte Adhesion Molecule-1 (ELAM-1) to inhibit expression of the protein product revealed that there were no generalized rules for the selection of the antisense oligonucleotides that exhibited optimum or even sub-optimum activity (Table 1). The mRNA for ELAM-1 is 3,863 nucleotides in length. The length of the 5'-untranslated region is 141 nucleotides, the coding region 1,830 nucleotides long, and the 3'-untranslated region is 1,892 nucleotides in length. Assuming that one wishes to design antisense oligonucleotides 21 nucleotides in length there are 3,842 potential 21-mers that could be synthesized. However, many of these 3,842 oligonucleotides will not exhibit sufficient activity to inhibit translation of the ELAM-1 mRNA. Experimental determination of the capacity for 22 different antisense oligonucleotides to inhibit ELAM-1 protein synthesis revealed that approximately 13% of the synthesized oligonucleotides did not significantly inhibit ELAM-1 protein synthesis (greater than 50% inhibition at 0.1 µM) as depicted in FIG. 1 where the long bar denotes the mRNA sequence of human ICAM-1. The 5'cap, untranslated regions (UTR), start codon (AUG), coding sequence, termination codon (UAA) and polyadenylated tail are enumerated above the bar. Gray areas denote intron regions. The shorter bars denote oligodeoxynucleotides (ODN) that have been evaluated for their ability to suppress expression of ICAM-1 in human umbilical vein endothelial cells. The code number for each ODN is printed just below the bars. All ODNs were evaluated at 0.1 µM. Bold bars represent ODNs that inhibit ICAM-1 expression greater than 50%

In these experiments, antisense oligonucleotides were added to human umbilical vein endothelial cells (HUVEC) in the presence of 10 µg/ml Lipofectin (Life Technologies, Gaithersburg, Md.) in serum free media for 4 hours. Media containing oligonucleotide was removed and media containing 10% fetal calf serum was added.

TABLE 1

ELAM-1 ANTISENSE OLIGONUCLEOTIDES

| Oligo-nucleotide[1] | Location[2] | Length (Nucleotides) | % GC[3] | Tm[4] | % Inhibition[5] |
|---|---|---|---|---|---|
| GM1516 | 103–123 | 21 | 47.6 | 66.2 | 89 |
| GM1517 | 128–148 | 21 | 38.1 | 58.6 | 68 |
| GM1818 | 103–120 | 18 | 50.0 | 59.9 | 49 |
| GM1819 | 118–132 | 15 | 46.7 | 43.5 | 37 |
| GM1820 | 138–155 | 18 | 44.4 | 52.4 | 4 |
| GM1821 | 126–140 | 15 | 40.0 | 34.8 | 8 |
| GM1836 | 126–146 | 21 | 33.3 | 54.6 | 22 |
| GM1837 | 127–147 | 21 | 38.1 | 56.1 | 23 |
| GM1838 | 132–152 | 21 | 38.1 | 60.4 | 0 |

[1]Oligonucleotides - modified using phosphorothioate chemistry.
[2]Location - represents the number of nucleotides in the mRNA that are complementary to the antisense sequence.
[3]% GC - represents the percentage of guanine and cytosine nucleo-bases comprising the total nucleotide composition of the oligonucleotide.
[4]Tm - represents the predicted Tm (represents the temperature, °C., where the strands are half dissociated or denatured. These values are predicted using the nearest neighbor approach (Breslauer et al., 1986, Proc. Natl. Acad. Sci. 83: 3746–3750 and Freier, et al., 1986, Proc. Natl. Acad. Sci. 83: 9373–9377).
[5]% Inhibition - represents the percent decrease in IL-1β (10 U/ml)-induced ELAM-1 protein expression. Cells (human umbilical vein endothelial) were treated with 100 nM oligonucleotide prior to ELAM-1 induction. ELAM-1 expression was determined 24 hours post-induction.

Approximately 16 hours later, ELAM-1 protein synthesis was induced by the addition of either IL-1β (interleukin-1β at 10 U/ml) or LPS (lipopolysaccharide at 0.5 µg/ml). These compounds caused marked induction of ELAM-1 protein expression as determined by a radio-immuno assay. Evaluation of the data demonstrated that there were no rules or obvious sequence locations that consistently predict active antisense oligonucleotides. For example, a series of phosphorothioate-modified oligonucleotides directed against the ELAM-1 mRNA sequence between nucleotides 103–155 exhibited an extremely varied capacity to inhibit the expression of the ELAM-1 protein (from 0–89% inhibition). Oligonucleotide GM1517, an oligonucleotide 21 nucleotides (21-mer) in length, inhibited IL-1β-induced expression (68% inhibition at 0.1 mM). GM1517 was designed to hybridize to ELAM-1 mRNA nucleotides 128–148. Three other 21-mer phosphorothioate oligonucleotides that were complementary to the ELAM-1 mRNA near GM1517 did not exhibit the capacity to similarly inhibit ELAM-1 expression. GM1836 (complementary to nucleotides 126-146), GM1837 (complementary to nucleotides 127–147) and GM1838 (complementary to nucleotides 132–152) exhibited reduced activity at 0.1 mM (22%, 23%, and 0% inhibition, respectively). There were no obvious reasons for this range of potency for the four oligonucleotides. All four of the oligonucleotides were complementary to sequences that spanned the initiation codon (AUG located at nucleotides 141–143). All four oligonucleotides were designed to hybridize to the only characterized semi-conserved translation regulation sequence located near the initiation codon, the Kozak sequence (Kozak, M., 1987, J. Mol. Biol. 196: 947–950). The differences observed with these four oligonucleotides could not be predicted based upon the analysis of the abilities to form hybrids with the mRNA. Examination of the predicted Tm (based upon the nearest neighbor approach) for these four antisense oligonucleotides reveals that the active antisense sequence, GM1517 has predicted Tm (that temperature, in degrees C, where the strands are half dissociated or denatured) of 58.6° C. The Tms for the less active sequences, GM1836 and GM1837 are 54.6 and 56.1° C. Oligonucleotide GM1838, which failed to produce any detectable inhibition of IL-1β-induced ELAM-1 expression has the highest predicted Tm, 60.4° C. A 15-mer phosphorothioate antisense oligonucleotide, GM1819 (designed to be complementary to nucleotides 118–132) demonstrated a greater inhibition of ELAM-1 expression (37%) than did three of the 21-mers described above. GM1819 has a predicted Tm of 43.5° C. and it does not hybridize to the AUG or Kozak sequences. Thus, antisense activity or lack of activity can not be determined based upon their ability to hybridize to the translation start codon or regulatory sequences near the start codon and determination of Tm (or G/C content) is not sufficient to predict potentially active antisense oligonucleotides.

Figure 2:
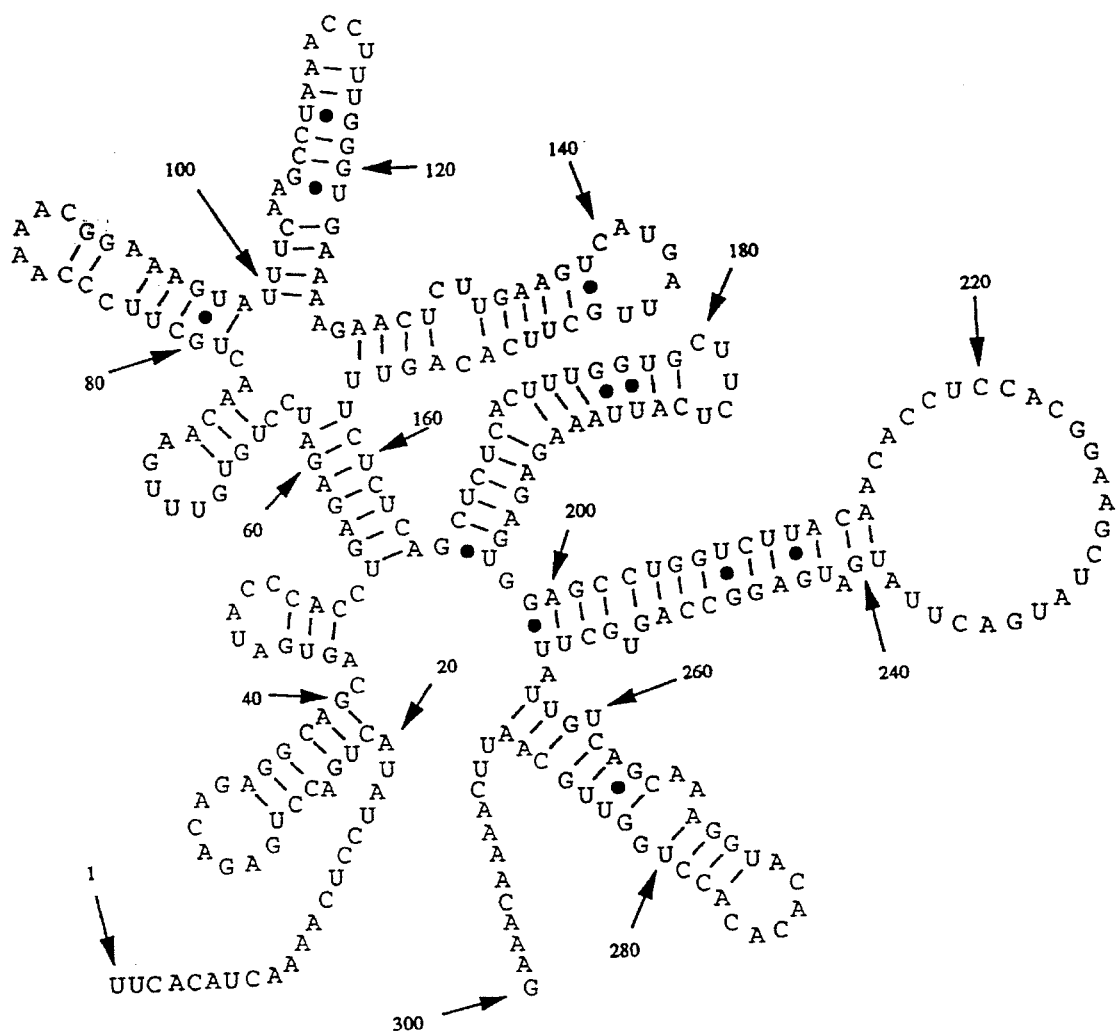
FIG. 2 is a predicted secondary structure for 5'-untranslated end (nucleotides 1–300) of human ELAM-1 mRNA (free energy for formation=–54.2 kcal/mole)

Based upon the above discussions of antisense activity for oligonucleotides that are similar in length and complementary to the same nucleotides, there are no rational explanations or rules that would predict active sequences. There have been suggestions that mRNA secondary structures might be important factors that would make the selection of an active antisense oligonucleotide obvious. FIG. 2 shows the secondary structure that would be present in nucleotides 1–300 for the 5' end of ELAM-1 mRNA. The predicted free energy for this structure is –54.2 kcal/mole. There does not appear to be any obvious feature of the mRNA secondary structure that would suggest that oligonucleotides complementary to that sequence would exhibit antisense activity. The four oligonucleotides discussed above, GM1517, GM1836, GM1837 and GM1838 all are complementary to nucleotides contained within a predicted stem-loop structure in the ELAM-1 mRNA (nucleotides 128–157). While all of these oligonucleotides were designed to bind with relatively similar thermodynamic stability (predicted Tms range from 54.6° to 60.4° C.) and to sequences contained within the predicted stem structure, they exhibited differences in their ability to inhibit expression.

Based upon the above discussion of the data obtained in the analysis of antisense oligonucleotides targeting the mRNA for human ELAM-1, there are no obvious regions of a target mRNA that can be predicted to be effective targets for antisense oligonucleotideinduced down regulation of protein synthesis. The selection of any specific oligonucleotide sequence that exhibits antisense activity requires rigorous experimental evaluation of a number of antisense sequences. The experimental determination for ELAM-1 antisense sequences suggest that there are only generalized regions of the mRNA for selecting an active antisense oligonucleotides that can significantly inhibit the expression of a particular protein. Thus without any rules or generalizations for predicting active antisense oligonucleotides, many different regions of the human ELAM-1 mRNA must be experimentally examined for selection of active antisense sequences. After analysis of this data only those oligonucleotides that exhibit significant inhibition of ELAM-1 protein expression are selected for further analysis.

The following chart provides a correlation between the compound number, the Sequence ID number and the Sequence. The location of support in the specification (beside the Sequence ID number) is also provided.

| Seq. No. | Compound ID No. | Sequence | Support |
|---|---|---|---|
| 1 | GM1515 | GTTTAAGGCA GCATCCTAAG A | FIG. 1 |
| 2 | GM1516 | TCACCCAAAG GTTTAGGCCTT G | Table 1, FIG. 1 |
| 3 | GM1517 | GCAATCATGA CTTCAAGAGT T | Table 1, FIG. 1 |
| 4 | GM1518 | GTTCACAACT GAAAAACAAA C | FIG. 1 |
| 5 | GM1519 | GCATGTCACA GCTGTAACAA A | FIG. 1 |
| 6 | GM1520 | TGAAGTCAGC CAAGAACAGC T | FIG. 1 |
| 7 | GM1521 | CGTTCTGCAC TTACCGTTTT G | FIG. 1 |
| 9 | GM1812 | CAGCCAAGAA CAGT | FIG. 1 |
| 10 | GM1813 | CAGCCAAGAA CAGCTGG | FIG. 1 |
| 11 | GM1814 | GATGTGAAGT CAGCCAA | FIG. 1 |
| 12 | GM1818 | CCCAAAGGTT TAGGCTTG | Table 1, FIG. 1 |
| 13 | GM1819 | GAGTTCTTTT CACCC | Table 1, FIG. 1 |

The following examples illustrate the principles and practices of the invention and are not intended to limit its scope in any way.

EXAMPLE 1

This example describes the preparation and use of a series of oligonucleotides whose base sequences are complementary to sequences contained in the human ELAM-1 mRNA transcript. The oligonucleotides are synthesized on an automated DNA synthesizer using standard techniques practiced in the art.

Phosphorothioate oligonucleotides are synthesized using standard procedures (Iyer, R.P. et al. (1990) J. Amer. Chem. Soc. 112: 1253–1254, 1990). A sequence of one of these phosphorothioate oligonucleotides, complementary to the 5' untranslated region and translation initiation codon, is 5'-GCA ATC ATG ACT TCA AGA GTT-3' where the translation initiation codon is underlined. This oligonucleotide is known by the name GM1517. GM1517 is prepared for delivery to the vasculature using an i.v. solution containing the oligonucleotide. The antisense oligonucleotide is presented to the lining of the vasculature, the endothelium cells expressing ELAM-1, taken up by the cells and forms a stable heteroduplex with the mRNA transcript that codes for ELAM-1. This hybridization of the oligonucleotide to the mRNA results in a down-regulation of ELAM-1 synthesis. Due to the down-regulation of ELAM-1 synthesis, there is a reduction in the cell membrane presentation of ELAM-1. With a down-regulation of ELAM-1 there is a reduction in the adhesion of leukocytes to the endothelium, and thus, a reduction in the inflammatory response.

The frequency and duration of i.v. oligonucleotide therapy, concentration of oligonucleotide in the i.v. fluid will vary from patient to patient and can be determined by the prescribing physician. While the inflammatory response is being abated by the antisense oligonucleotide therapy, the use of standard therapies are used to control the bacterial or other infection that resulted in the manifestation of the septic shock.

EXAMPLE 2

The inhibitors of this invention are administered, preferably by intravenous infusion in a suitable pharmaceutical carrier, in a range of 0.01 to 500 mg/Kg body weight preferably in the range of 0.05 to 250 mg/Kg body weight and most preferably in the range of 0.15 to 50 mg/kg body weight. The oligonucleotide analogues do not rapidly enter cells. To improve cell entry, the oligonucleotide can be delivered together with a membrane permeablizing agent like polyoxyethylene sorbitan mono-oleate (Tween 80) or polyethylene glycol 300 molecular weight (PEG 300). Alternatively, the oligonucleotide solutions can be prepared by including it as an encapsulated material in a liposome suspension by any of several techniques. Alternatively, oligonucleotides are conjugated to compounds which expand the lifetime of the material in the circulating blood and enhance endothelial cell uptake. An example of a suitable conjugation moiety would be the vitamin folate. Obviously, many modifications and variations of the present invention are possible in light of the above teachings. It is therefore to be understood that, within the scope of the appended claims, the invention may be practiced otherwise than as specifically described.

What is claimed is:

1. A synthetic oligonucleotide having a nucleotide sequence of from 15 to 21 bases selected from the group consisting of the sequences:

GTT TAA GGC AGC ATC CTA AGA (SEQ ID No. 1);
TCA CCC AAA GGT TTA GGC TTG (SEQ ID No. 2);
GCA ATC ATG ACT TCA AGA GTT (SEQ ID No. 3);
GTT CAC AAC TGA AAA ACA AAC (SEQ ID No. 4);
GCA TGT CAC AGC TGT AAC AAA (SEQ ID No. 5);
TGA AGT CAG CCA AGA ACA GCT (SEQ ID No. 6);
CGT TCT GCA CTT ACC GTT TTG (SEQ ID No. 7);
CAG CCA AGA ACA GCT (SEQ ID No. 9);
CAG CCA AGA ACA GCT GG (SEQ ID No. 10);
GAT GTG AAG TCA GCC AA (SEQ ID No. 11);
CCC AAA GGT TTA GGC TTG (SEQ ID No. 12), and
GAG TTC TTT TCA CCC (SEQ ID No. 13).

2. The oligonucleotide according to claim 1 wherein the oligonucleotide has the sequence 5-GCA ATC ATG ACT TCA AGA GTT-3 (SEQ ID No. 3).

3. The ofigonucleotide according to claim 1 wherein the oligonucleoride has the sequence GTT TAA GGC AGC ATC CTA AGA (SEQ ID No. 1).

4. The oligonuclcotide according to claim 1 wherein the oligonuclcotide has the sequence TCA CCC AAA GGT TTA GGC TTG (SEQ ID No. 2).

5. The oligonucleotide according to claim 1 wherein oligonucleotide comprises the sequence GTT CAC AAC TGA AAA ACA AAC (SEQ ID No. 4).

6. The oligonucleotide according to claim 1 wherein the oligonucleotide has the sequence GCA TGT CAC AGC TGT AAC AAA (SEQ ID No. 5).

7. The oligonucleotide according to claim 1 wherein the oligonucleotide has the sequence TGA AGT CAG CCA AGA ACA GCT (SEQ ID No, 6).

8. The oligonucleotide according to claim 1 wherein the oligonucleotide has the sequence CGT TCT GCA CTT ACC GTT TTG (SEQ ID No. 7).

9. The oligonucleotide according to claim 1 wherein the oligonucleotide has the sequence CAG CCA AGA ACA GCT (SEQ ID No. 9).

10. The oligonucleotide according to claim 1 wherein the oligonucleotide has the sequence CAG CCA AGA ACA GCT GG (SEQ ID No. 10).

11. The oligonucleotide according to claim 1 wherein the oligonucleotide has the sequence GAT GTG AAG TCA GCC AA (SEQ ID No. 11).

12. The oligonuclcotidc according to claim 1 wherein the oligonucleotide has the sequence CCC AAA GGT TTA GGC TTG (SEQ ID No. 12).

13. The oligonucleotide according to claim 1 wherein the oligonucleotide has the sequence GAG TTC TTT TCA CCC (SEQ ID No. 13).

* * * * *

SEQUENCE LISTING ( 1 ) GENERAL INFORMATION:

( i i i ) NUMBER OF SEQUENCES: 13

( 2 ) INFORMATION FOR SEQ ID NO:1:

-continued (i) SEQUENCE CHARACTERISTICS:
    (A) LENGTH: 21 base pairs
    (B) TYPE: nucleic acid
    (C) STRANDEDNESS: single
    (D) TOPOLOGY: linear (iii) HYPOTHETICAL: NO (iv) ANTI-SENSE: YES (xi) SEQUENCE DESCRIPTION: SEQ ID NO:1:

GTTTAAGGCA GCATCCTAAG A                              21

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:2:

TCACCCAAAG GTTTAGGCTT G                              21

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:3:

GCAATCATGA CTTCAAGAGT T                              21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:4:

GTTCACAACT GAAAAACAAA C                              21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:5:

GCATGTCACA GCTGTAACAA A 21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:6:

TGAAGTCAGC CAAGAACAGC T 21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:7:

CGTTCTGCAC TTACCGTTTT G 21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:8:

GAAATACTTT CCTGGGGAGA T 21

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:9:

CAGCCAAGAA CAGCT 15

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (iii) HYPOTHETICAL: NO (i v) ANTI-SENSE: YES (x i) SEQUENCE DESCRIPTION: SEQ ID NO:10:

CAGCCAAGAA CAGCTGG 17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i i) HYPOTHETICAL: NO (i v) ANTI-SENSE: YES (x i) SEQUENCE DESCRIPTION: SEQ ID NO:11:

GATGTGAAGT CAGCCAA 17

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i i) HYPOTHETICAL: NO (i v) ANTI-SENSE: YES (x i) SEQUENCE DESCRIPTION: SEQ ID NO:12:

CCCAAAGGTT TAGGCTTG 18

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i i) HYPOTHETICAL: NO (i v) ANTI-SENSE: YES (x i) SEQUENCE DESCRIPTION: SEQ ID NO:13:

GAGTTCTTTT CACCC 15